(12) United States Patent
Rouleau et al.

(10) Patent No.: US 6,828,430 B1
(45) Date of Patent: Dec. 7, 2004

(54) SHORT GCG EXPANSIONS IN THE PAB II GENE FOR OCULOPHARYNGEAL MUSCULAR DYSTROPHY AND DIAGNOSTIC THEREOF

(75) Inventors: Guy A. Rouleau, Montreal (CA); Bernard Brais, Outremont (CA)

(73) Assignee: McGill University, Montreal (CA)

( * ) Notice: Subject to any disclaimer, the term of this patent is extended or adjusted under 35 U.S.C. 154(b) by 337 days.

(21) Appl. No.: 09/590,211

(22) Filed: Jun. 8, 2000

Related U.S. Application Data (63) Continuation of application No. PCT/CA98/01133, filed on Dec. 7, 1998.

(30) Foreign Application Priority Data

Dec. 9, 1997  (CA) .............................................. 2218199

(51) Int. Cl.[7] .......................... C07H 21/02; C07H 21/04
(52) U.S. Cl. ................. 536/23.1; 536/24.33; 536/24.31
(58) Field of Search .............................. 536/23.1, 23.4, 536/23.5, 24.33; 435/325, 6

(56) References Cited

FOREIGN PATENT DOCUMENTS

| WO | WO98/31800 | 7/1998 |
| WO | WO99/29896 | 6/1999 |

OTHER PUBLICATIONS

Genebank deposit AFO26029, Feb. 20, 1998.*
Grewal et. al.; Genetic mapping and haplotype analysis of oculopharyngeal muscular dystrophy, 1998, Neoro–Report 9: 961–965.*
Stajich et.al.; Confirmation of linkage of oculopharyngeal . . . existence of a second causal mutation, 1997, Neuromuscular Disorders 7: S75–S81.*
Akarsu et. al.; Genomic structure of HOXD13 gene: a nine polyalanine duplication causes synploydactyly in two unrelated families, 1996, Human Molecular Genetics, vol. 5: 945–952.*
Brais et.al.; Oculopharyngeal Muscular Dystrophy, 1999, Seminars in Neurology, vol. 19: 59–66.*
Brais et.al.; Short GCG expansions in the PABP2 gene cause oculopharyngeal muscular dystrophy, 1999, Nature Genetics, vol. 18: 164–167.*
Tomè M.S., et al., "Nuclear Inclusions in Oculopharyngeal Dystrophy", *Acta Neuropathologica*, 49:85–87 (1980).
Lafrenière R.G., et al., "Unstable insertion in the 5' flanking region of the cystatin B gene is the most common mutation in progressive myoclonus epilepsy type 1, EPM1", *Nature Genetics*, 15:298–302 (Mar. 1997).
Rommens J.M., et al., "Towards a Transcriptional Map of the q21–q22 Region of Chromosome 7", *Plenum Press*, pp:65–79 (1994).

Akarsu, A.N., et al., "Genomic Structure of HOXD13 Gene: A Nine Polyalanine Duplication Causes Synpolydactyly in Two Unrelated Families," *Human Molecular Genetics*, 5(7): 945–952 (1996).
Bienroth, S, et al., "Assembly of a Processive Messenger RNA Polyadenylation Complex," *The EMBO Journal*, 12(2): 585–594 (1993).
Brais, B., et al., "Using the Full Power of Linkage Analysis in 11 French Canadian Families to Fine Map the Oculopharyngeal Muscular Dystrophy Gene," *Neuromuscular Disorder* 7(1):S70–S74 (1997).
Brais, B, et al., "The Oculopharyngeal Muscular Dystrophy Locus Maps to the Region of the Cardiac α and β Myosin Heavy Chain Genes on Chromosome 14q11.2–q13," *Human Molecular Genetics*, 4(3): 429–434 (1995).
Davies, S.W., "Formation of Neuronal Intranuclear Inclusions Underlies the Neurological Dysfunction in Mice Transgenic for the HD Mutation," *Cell*, 90:537–548 (1997).
DiFiglia, M, et al., "Aggregation of Huntingtin in Neuronal Intranuclear Inclusions and Dystrophic Neurites in Brain," *Science*, 277: 1990–1993 (1997).
Evans, G.A, et al., "High Efficiency Vectors for Cosmid Microcloning and Genomic Analysis," *Gene*, 79:9–20 (1989).
Forood, B., et al., "Formation of an Extremely Stable Polyalanine β–Sheet Macromolecule," *Biochem. And Biophysical Res. Communications*, 211(1): 7–13 (1995).
Krause, S., et al., "Immunodetection of Poly(A) Binding Protein II in the Cell Nucleus," *Experimental Cell Res.*, 214: 75–82 (1994).
Mundlos, S., et al., "Mutations Involving the Transcription Factor CBFA1 Cause Cleidocranial Dysplasia," *Cell*, 89: 773–779 (1997).
Editorials, "DNA–Triplet Repeats and Neurologic Disease," *The New England Journal of Med.*, 335(16): 1222–1224 (1996).
Scherzinger, E., et al, "Huntingtin–Encoded Polyglutamine Expansions Form Amyloid–Like Protein Aggregates In Vitro and In Vivo," *Cell* 90: 549–558 (1997).

(List continued on next page.)

*Primary Examiner*—Joe Woitach
(74) *Attorney, Agent, or Firm*—Hamilton, Brook, Smith & Reylonds, P.C.

(57) ABSTRACT

The present invention relates to a human PAB II gene containing transcribed polymorphic GCG repeat, which comprises a sequence as set forth in SEQ ID NO:18, which includes introns and flanking genomic sequence. Allelic variants of GCG repeat of the human PAB II gene are associated with a disease related with protein accumulation in the nucleus, such as polyalanine accumulation, or with swallowing difficulties, such as oculopharyngeal muscular dystrophy. The present invention also relates to a method for the diagnosis of a disease associated with protein accumulation in the nucleus, which comprises the steps of: a) obtaining a nucleic acid sample of a patient; and b) determining allelic variants of GCG repeat of the PAB II gene, and wherein long allelic variants are indicative of a disease related with protein accumulation in the nucleus.

17 Claims, 8 Drawing Sheets

OTHER PUBLICATIONS

Tome, M.S., et al., "Nuclear Inclusions in Oculopharyngeal Dystrophy," *Act Neuropathol.* 49: 85–87 (1980).

Muragaki, Y., et al., "Polyalanine Expansion in Synpolydactyly Might Result from Unequal Crossing–Over of HOXD13," *Science* 275: 406.

Wells, R.D., "Molecular Basis of Genetic Instability of Triplet Repeats," *The Journal of Biological Chem.* 271(6): 2875–2878 (1996).

Wahle, E., et al., "Mammalian Poly(A)–Binding Protein II," *J. of Biological Chem.*, 268(4): 2937–2945 (1993).

Wahle E., "A Novel Poly(A)–Binding Protein Acts As a Specificity Factor in the Second Phase of Messenger RNA Polyadenylation," *Cell*, 66: 759–768 (1991).

Nemeth, A., et al., "Isolation of Genomic and cDNA Clones Encoding Bovine Poly(A) Binding Protein II," *Nucleic Acids Res.*, 23(20): 4034–4041 (1995).

Riggins, G.J., et al. "Human Genes Containing Polymorphic Trinucleotide Repeats," *Nat Genet*, 2(3):186–191 (1992).

Brais, B., et al., "Short GCG Expansions in the PABP2 Gene Cause Oculopharyngeal Muscular Dystrophy," *Nature Genetics* 18: 164–167 (1998).

Lamartine, J. et al., "Cloning Sequencing and Chromosomal Assignment of a New cDNA Clone to Xq12–q13 and 14q11," EMBL Data Base Accession No. U12206 (1995).

"National Cancer Institute, Cancer Genome Anatomy Project (CGAP), Tumor Gene Index," EMBL Data Base Accession No. AA618589 (1997).

Sullivan, T.B.T., et al., "Oculopharyngeal Muscular Dystrophy (OPMD)—Report and Genetic Studies of an Australian Kindred," *Clinical Genetics*, 51: 52–55 (1997).

Bouchard, J.P. et al., "A Simple Test for the Detection of Dysphagia in Members of Families with Oculopharyngeal Muscular Dystrophy (OPMID)," Can.J. Neurol. Sci. 19(2):296–297 (1992).

* cited by examiner

FIG. 2A    FIG. 2B FIG. 2C FIG. 2D FIG. 2E (GCG)$_{6+n}$
expansions
N 2 3 4 5 6 7

GATC    FIG. 2G

OPMD dominant mutations:

N: ATGGCGGCGGCGGCGGCGGCAGCAGCA

ATGGCGGCGGCGGCGGCG(GCG)$_{2-7}$GCA

Polyalanine insertions:

N: MAAAAAAAAAGAAGGRGS

MAAAAAA(A)$_{2-7}$AAAAGAAG

FIG. 3

```
   1 aatgaaggtg gacacccaaa tagccccaat acaaatgcct gttcaatcaa ccaaacatct
  61 aagcagcaca tctatgtggt agcatattgc caggccgtga gactgcgaat ataaatagga
 121 accgcccctc atctgcaggc gctcacaacc tagttagcaa acagtaaaac aattaagcgc
 181 gccgtggaca taggcccact tgtcctggga aatgagggga agctggggtt tgcagtggtt
 241 tgattgaagg gggactacat gttagaggca cagactgggt gcaggtacac ccaaaggaac
 301 gagaagagtg gaaggaaaca acatccacac agtaaccaca tgctggcgta tcgaaggccg
 361 tgatttacgg ttttgagact ttacctcgcc agcaaagggg ggccagtctg ttagcggtgc
 421 agattggagg ggtgacattg gaagctgtcc aggaaaaaga aatggaact gggagcaga
 481 aggcctacgc aagagggcgg gacagacagg acttgtgact agtagctctg gactgaggaa
 541 tcctccctgc tttctggtgc gggagagcta gtggatgatg gtgccaataa cctggatggg
 601 gaaagtaagc tccctcctgg aatgcttcat tcacaacctc cattttcagc aacatcccat
 661 ctactggtgc ttcctggtcg agatacaagt ttcctgaaac tgctgctctg tttttgggcct
 721 cacccggcca acagctcact agctggcaag cagtagtatc aagatggcgg cccctagga
 781 ctggctagtc atgtgacctc gggtttccca agtttgaagc ccggcagtcc tttcggggc
 841 aaggttcacc tgtcacgaaa cgagtgtcac ccctccgact ctcgcaagcc aatcggcatc
 901 tgagactggg ccactgcggt gaggcgatcg gaagattggt cctttccagt cgcctagcta
 961 gggccaatca cggagcgtcc gggcccgccc gtaggccggg gagaagcagg
1021 aatatcgtca cagcgtggcg catacttcgc ctaaggactc gataggaggt gggacgcgtg
1081 ttgattgaca ggcagatttc tttgagaatt tggcagtg cccgccttag
1141 aggtgcgctt atttgattgc caagtaatat tcccaatgg agtactagct catggtgacg
```

FIG. 4A

```
1201  ggcaggcagc  ttgagctaat  gagtcctccg  tggccggcgc  agctctccac  atgccggggcg
1261  gcgggcccca  gtctgagcgg  cgatggcggc  ggcggcggcg  gcggcagcag  cagcggggggc
1321  tgcgggcggt  cgggctccg   ggcggggcg   gcggcgccat  cttgtgcccg  gggccggtgg
1381  ggaggccggg  gaggggccc   cggggggcgc  agggactac   gggaacggcc  tggagtctga
1441  ggaactggag  cctgctgagc  tgctgctgga  gcccgagccg  gagcccgagc  ccgaagagga
1501  gccgcccccgg  ccccgcgccc  ccccgggagc  tccgggcccct  gggcctggtt  cggagcccc
1561  cggcagccaa  gaggaggagg  aggagccggg  actggtcgag  ggtgacccgg  gggacggcgc
1621  cattgaggac  ccggtgagga  aggagggcga  gcgagcaggc  cggcgctgg   cgcgtcactg
1681  gaggcccaga  gctcggggcc  gcggtggcag  gcgggggtg   gggttgggcg  gggaataacg
1741  tggctgggcg  gggtcgggcc  gggatgggt   cagcgatcac  tacaaggggc  ccgactggct
1801  tgattcgggc  gtcacgggtg  cctagtgttg  ttctagagag  ggtagctttt  cttttatcac
1861  gaccctcgca  tggggcgagg  gaaatggccg  agcatggctg  aggcgcgctc  tggccgagag
1921  caggcacag   cccctgcgtt  ggttcctctt  aagctgtcct  ccataccctc  cccacttata
1981  ttaggagctg  gaagctatca  aagctcgagt  cagggagatg  gaggaagaag  ctgagaagct
2041  aaaggagcta  cagaacgagg  tagagaagca  gatgaatatg  agtccacctc  caggcaatgc
2101  tgagtaactg  gcggttgcac  gcggagcccg  ggttctcggg  ttggaagggt  tgtggggagg
2161  atggggaatg  tggggttaga  tactcggcac  cctggagctg  cttgtctgag  ctattatgac
2221  tgtgccgcgg  tcatagtccg  ttgtgtgttc  ctctgacctt  tgtgaggcag  aactgatatt
2281  ttggtggtgg  tagccttgtg  ctcccctttg  tcctgttata  attgtgttgc  tctttattct
2341  tagtctacgt  ctatctttct  ttggtagagg  ttgcgtgctc  gcatttgacc  ttcaaatcta
```

FIG. 4B

```
2401  atagtttttc  ctccaattgg  agacgcttta  ggattctaag  agaaagcaag  ctggaagggg
2461  tttcccttt   aaattctaga  aatgtggagt  ctcagcccac  ttaattttgc  tcactcttaa
2521  aagcatttca  accaaagcca  ttcattaggg  atttgatttg  gagggcagga  gggattccta
2581  tactgtttta  agtgtgtatt  aattctttca  atttatcgaa  ttattagtg   agtaacctgc
2641  tatgcactag  gcactattct  cggcttgtgg  gtacagcagg  gaacagcaca  gaccaaaatc
2701  tttgccttca  ctgagcttat  gggatagtgc  tggtggtgga  agtgcaacat  attggtcaag
2761  tagaaaacaa  gtgtgtggtt  tttgtaaaaa  attattttt   cctgatagct  ggcccggtga
2821  tcatgtccat  tgaggagaag  atggaggctg  atgcccgttc  catctatgtt  ggcaatgtga
2881  cgtactgggg  ctctgactgg  ggttgggggc  aagttctcct  tttgggaat   tatttaatag
2941  tcctgaaaga  acatctccgg  gatagatgtg  gttttgggtg  tgggggagt   gtgggaagga
3001  ggttaaaggt  aatggaatga  tcagtaatca  gcaaaggctc  tgggtttgga  aggaaaagag
3061  attaattcct  caaattacca  gatttcatgt  gctttgttgt  atgatggccc  agaccaaagg
3121  ctcggaggg   ttcttttttgag acaggaattt gcctggtgcc  tgtgaaattt  ttctccctctc
3181  atcaggtgga  ctatggtgca  acagcagaag  agctggaagc  tcactttcat  ggctgtgtt
3241  cagtcaaccg  tgttaccata  ctgtgtgaca  aatttagtgg  ccatcccaaa  ggtaaagtaa
3301  aggggagtaa  gttgagataa  tttaaattac  agtgtacaaa  tagataaatt  atgtttata
3361  ttgagcagta  agttatttgg  tgttaacaca  ggtgatctgt  gtcatttaag  atcatggcat
3421  taatgtttgat atatcaggag  ttgcacctaa  atgtcttcag  aggccagata  acaaaaatga
3481  aggctagatg  tgggtgggat  tacgaactag  aagggggagg  gcagcttcta  cttggcctat
3541  tatggcatat  ggaaattcag  gccctgtgtg  tcttattttt  acaaatttca  aagagtagct
```

FIG. 4C

```
3601  ggaaatttta  aaatttaaat  gatttcgaat  gattgaaatt  ttccatttag  aagaattttg
3661  acaaataaaa  aatataactg  cattgtagcc  caaaacgaag  catgcctgca  ggttgaattt
3721  gacctgtgag  gtatttgtaa  cctcagagag  atacaatgac  aattcttttc  aggtttgcgt
3781  atatagagtt  ctcagacaaa  gagtcagtga  ggacttcctt  ggccttagat  gagtccctat
3841  ttagaggaag  gcaaatcaag  gtaagcctat  gtccattgct  gttctagttg  tgtataaact
3901  ctccaggttg  cctttaaggc  tatcatttgt  tcatctctga  ctcaggtgat  cccaaaacga
3961  accaacagac  caggcatcag  cacaacagac  cggggttttc  cacgagcccg  ctaccgcgcc
4021  cggaccacca  actacaacag  ctcccgctct  cgattctaca  gtggttttaa  cagcaggccc
4081  cgggtcgcg   tctacaggtc  aggatagatg  ggctgctcct  ctttccccg   cctcccgtga
4141  gccccgtatg  cttcctcctc  tctggtctga  ggaacctccc  tccccccacc  cctccccgtg
4201  gtcttcagga  actttgtctc  ctgcctgtgc  aggttgagga  aggtagttgc  aggccaggcc
4261  agaaggcagc  ctcatcatct  tttctgcagt  agaaattggt  gataaggct   gcatccctcc
4321  cttggttcaa  agaggcttcc  accccagcc   ttttttttct  tgggagttgg  tgcatttga
4381  aggtgtttgc  ggacaaaact  gggaggaaca  gggcctccag  gaagttgaaa  gcactgcttg
4441  gacatttgtt  acttttttcg  gagttaggga  gggattgaag  actgaacctc  ccttggaaga
4501  ataccagagg  ctagctagtt  gatcctccca  acagccttgt  gggaggattt  tgagatactt
4561  attcttatt   tgagccagtc  ttgcaaggtt  aacttctcac  tgggcctagt  gtggtncca
4621  ggtttttgcc  ttgcttcact  tctgtctcta  catttaaata  gacgggttag  gcatataaac
4681  cttggctttt  cataagctct  acctgcctat  cccaggagt   tagggaggat  ctatttgtga
4741  agcccctagg  gtttaaaaac  tgtggaggac  tgaaaaactg  gataaaaagg  gggtcctttt
```

FIG. 4D

```
4801 ccttgcccct gtctctcact cagatgcgct tcttttttcgc cactgttttgg caaagtttttc
4861 tgttaagccc cctccccct gcccagttc tccagtgtc gttactatt ctgggatcat
4921 gggtcggtt ttaggacact tgaacactc ttcccccc ttccttcac agtaactggg
4981 gcagggcct acgggagg gcttgtactg aactatctag tgatcacgtt aacacctaac
5041 tctccttctt tcttccagg gccggctag agcgacatca tggtattccc cttactaaaa
5101 aaagtgtgta ttaggaggag agagaggaaa aaagaggaaa agagaggaaa aaaaagaat
5161 taaaaaaaaa aaaagaaaa acagaagatg acccttgatgg aaaaaaaata tttttaaaa
5221 aaagatata ctgtggaagg gggagaatc ccataactaa ctgctgagga gggacctgct
5281 ttgggagta gggaaggcc caggagtgg ggcaggggc tgcttattca ctctgggat
5341 tcgccatgga cacgtctcaa ctgcgcaagc tgcttgccca tgtttccctg ccccttcac
5401 ccccttgggc ctgctcaagg gtaggtgggc gtgggtggta ggagggttt ttttacccag
5461 ggctctggaa ggacaccaa ctgttctgct tgttaccttc cctccccgtct tctcctcgcc
5521 tttcacagtc ccctcctgcc cagccagtc taccaccac cccaccctc
5581 tttctccggc tccctgcccc tccagattgc ctggtgatct atttttgttc ctttgtgtt
5641 tctttttctg tttgagtgt cttctttgc aggtttctgt agccggaaga tctccgttcc
5701 gctcccagcg gctccagtgt aaattcccct tccccctggg gaaatgcact accttgtttt
5761 ggggtttta ggtccagttt tgttttcag ttgttttgtt tttttgtt tttttttcc
5821 tttgccttt ttccctttta tttggaggga atgggaacag gtgggaacag ggaggtggga
5881 ggtggattt gtttatttt ttagctcatt tccaggggtg ggaattttt tttaatatgt
5941 gtcatgaata aagttgtttt tgaaataaa aaaaaaaaa aaaaaaaaaa aaaaaaaaa
6001 aa
```

FIG. 4E

SEQUENCE LISTING

<160> NUMBER OF SEQ ID NOS: 21

<210> SEQ ID NO 1
<211> LENGTH: 30
<212> TYPE: DNA
<213> ORGANISM: Homo sapiens

<400> SEQUENCE: 1
atggcggcgg cggcggcggc ggcagcagca         30

<210> SEQ ID NO 2
<211> LENGTH: 24
<212> TYPE: DNA
<213> ORGANISM: Homo sapiens

<400> SEQUENCE: 2
atggcggcgg cggcggcggc ggca         24

<210> SEQ ID NO 3
<211> LENGTH: 27
<212> TYPE: DNA
<213> ORGANISM: Homo sapiens

<400> SEQUENCE: 3
atggcggcgg cggcggcggc ggcggca         27

<210> SEQ ID NO 4
<211> LENGTH: 30
<212> TYPE: DNA
<213> ORGANISM: Homo sapiens

<400> SEQUENCE: 4
atggcggcgg cggcggcggc ggcggcggca         30

<210> SEQ ID NO 5
<211> LENGTH: 33
<212> TYPE: DNA
<213> ORGANISM: Homo sapiens

<400> SEQUENCE: 5

-continued atggcggcgg cggcggcggc ggcggcggcg gca                33

<210> SEQ ID NO 6
<211> LENGTH: 36
<212> TYPE: DNA
<213> ORGANISM: Homo sapiens

<400> SEQUENCE: 6
atggcggcgg cggcggcggc ggcggcggcg gcggca             36

<210> SEQ ID NO 7
<211> LENGTH: 39
<212> TYPE: DNA
<213> ORGANISM: Homo sapiens

<400> SEQUENCE: 7
atggcggcgg cggcggcggc ggcggcggcg gcggcggca          39

<210> SEQ ID NO 8
<211> LENGTH: 42
<212> TYPE: DNA
<213> ORGANISM: Homo sapiens

<400> SEQUENCE: 8
atggcggcgg cggcggcggc ggcggcggcg gcggcggcgg ca      42

<210> SEQ ID NO 9
<211> LENGTH: 45
<212> TYPE: DNA
<213> ORGANISM: Homo sapiens

<400> SEQUENCE: 9
atggcggcgg cggcggcggc ggcggcggcg gcggcggcgg cggca   45

<210> SEQ ID NO 10
<211> LENGTH: 19
<212> TYPE: PRT
<213> ORGANISM: Homo sapiens

<400> SEQUENCE: 10

Met Ala Ala Ala Ala Ala Ala Ala Ala Ala Gly Ala Ala Gly Gly
 1               5                  10                  15

Arg Gly Ser

<210> SEQ ID NO 11
<211> LENGTH: 16
<212> TYPE: PRT
<213> ORGANISM: Homo sapiens

<400> SEQUENCE: 11

Met Ala Ala Ala Ala Ala Ala Ala Ala Ala Ala Gly Ala Ala Gly
 1               5                  10                  15

<210> SEQ ID NO 12
<211> LENGTH: 17
<212> TYPE: PRT
<213> ORGANISM: Homo sapiens

<400> SEQUENCE: 12

Met Ala Ala Ala Ala Ala Ala Ala Ala Ala Ala Ala Gly Ala Ala
 1               5                  10                  15

Gly

<210> SEQ ID NO 13
<211> LENGTH: 18
<212> TYPE: PRT
<213> ORGANISM: Homo sapiens

<400> SEQUENCE: 13

Met Ala Ala Ala Ala Ala Ala Ala Ala Ala Ala Ala Ala Ala Gly Ala
 1               5                  10                  15

Ala Gly

<210> SEQ ID NO 14
<211> LENGTH: 19
<212> TYPE: PRT
<213> ORGANISM: Homo sapiens

<400> SEQUENCE: 14

Met Ala Ala Ala Ala Ala Ala Ala Ala Ala Ala Ala Ala Ala Ala Gly
 1               5                  10                  15

Ala Ala Gly

<210> SEQ ID NO 15
<211> LENGTH: 20
<212> TYPE: PRT
<213> ORGANISM: Homo sapiens

<400> SEQUENCE: 15

Met Ala Ala Ala Ala Ala Ala Ala Ala Ala Ala Ala Ala Ala Ala Ala
 1               5                  10                  15

Gly Ala Ala Gly
        20

<210> SEQ ID NO 16
<211> LENGTH: 21
<212> TYPE: PRT
<213> ORGANISM: Homo sapiens

<400> SEQUENCE: 16

Met Ala Ala Ala Ala Ala Ala Ala Ala Ala Ala Ala Ala Ala Ala Ala
 1               5                  10                  15

Ala Gly Ala Ala Gly
        20

<210> SEQ ID NO 17
<211> LENGTH: 22
<212> TYPE: PRT
<213> ORGANISM: Homo sapiens

<400> SEQUENCE: 17

Met Ala Ala Ala Ala Ala Ala Ala Ala Ala Ala Ala Ala Ala Ala Ala
 1               5                  10                  15

Ala Ala Gly Ala Ala Gly
        20

<210> SEQ ID NO 18
<211> LENGTH: 6002
<212> TYPE: DNA
<213> ORGANISM: Homo sapiens
<220> FEATURE:
<221> NAME/KEY: misc_feature
<222> LOCATION: (4616)...(4616)
<223> OTHER INFORMATION: n= A,T,C, or G

<400> SEQUENCE: 18

-continued

| | |
|---|---|
| aatgaaggtg gacacccaaa tagccccaat acaaatgcct gttcaatcaa ccaaacatct | 60 |
| aagcagcaca tctatgtggt agcatattgc caggccgtga gactgcgaat ataaatagga | 120 |
| accgcccctc atctgcaggc gctcacaacc tagttagcaa acagtaaaac aattaagcgc | 180 |
| gccgtggaca taggcccact tgtcctggga aatgagggga agctggggtt tgcagtggtt | 240 |
| tgattgaagg gggactacat gttagaggca cagactgggt gcaggtacac ccaaaggaac | 300 |
| gagaagagtg gaaggaaaca acatccacaa agtaaccaca tgctggcgta tcgaaggccg | 360 |
| tgatttacgg ttttgagact ttacctcgcc agcaaagggg ggccagtctg ttagcggtgc | 420 |
| agattggagg ggtgacattg gaagctgtcc aggaaaaaga aaatggaact ggggagcaga | 480 |
| aggcctacgc aagagggcgg gacagacagg acttgtgact agtagctctg gactgaggaa | 540 |
| tcctccctgc tttctggtgc gggagagcta gtggatgatg gtgccaataa cctggatggg | 600 |
| gaaagtaagc tccctcctgg aatgcttcat tcacaacctc cattttcagc aacatcccat | 660 |
| ctactggtgc ttcctggtcg agatacaagt ttcctgaaac tgctgctctg ttttgggcct | 720 |
| cacccggcca acagctcact agctggcaag cagtagtatc aagatggcgg ccccctagga | 780 |
| ctggctagtc atgtgacctc gggtttccca agtttgaagc ccggcagtcc tttcggggc | 840 |
| aaggttcacc tgtcacgaaa cgagtgtcac cccttcgact ctcgcaagcc aatcggcatc | 900 |
| tgagactggg ccactgcggt gaggcgatcg gaagattggt cctttccagt cgcctagcta | 960 |
| gggccaatca cggagcgtcc catacttcgc gggcccgccc gtaggccggg gagaagcagg | 1020 |
| aatatcgtca cagcgtggcg gtattattac ctaaggactc gataggaggt gggacgcgtg | 1080 |
| ttgattgaca gcagatttc cctaccggga tttgagaatt tggcgcagtg cccgccttag | 1140 |
| aggtgcgctt atttgattgc caagtaatat tccccaatgg agtactagct catggtgacg | 1200 |
| ggcaggcagc ttgagctaat gagtcctccg tggccggcgc agctctccac atgccgggcg | 1260 |
| gcgggccccca gtctgagcgg cgatggcggc ggcggcggcg gcggcagcag cagcgggggc | 1320 |
| tgcgggcggt cggggctccg ggccggggcg gcggcgccat cttgtgcccg ggccggtgg | 1380 |
| ggaggccggg gagggggccc cggggggcgc agggggactac gggaacggcc tggagtctga | 1440 |
| ggaactggag cctgaggagc tgctgctgga gcccgagccg gagcccgagc ccgaagagga | 1500 |
| gccgccccgg ccccgcgccc ccccgggagc tccgggccct gggcctggtt cgggagcccc | 1560 |
| cggcagccaa gaggaggagg aggagccggg actggtcgag ggtgacccgg gggacggcgc | 1620 |
| cattgaggac ccggtgagga aggagggcga gcgagcaggc cggcggctgg cgcgtcactg | 1680 |
| gaggcccaga gctcgggcga gcggtggcag gcggggggtg gggttgggcg gggaataacg | 1740 |
| tggctggggc gggtcgggcc ggggatgggt cagcgatcac tacaagggc ccgactggct | 1800 |
| tgattcgggc gtcacgggtg cctagtgttg ttctagagag ggtagctttt cttttatcac | 1860 |
| gaccctcgca tggggcgagg gaaatggccg agcatggctg aggcgcgctc tggccgagag | 1920 |
| cagggcacag cccctgcgtt ggttcctctt aagctgtcct ccatacccctc cccacttata | 1980 |
| ttaggagctg gaagctatca aagctcgagt caggagatg gaggaagaag ctgagaagct | 2040 |
| aaaggagcta cagaacgagg tagagaagca gatgaatatg agtccacctc caggcaatgc | 2100 |
| tgagtaactg gcggttgcac gcggagcccg ggttctcggg ttggaagggt tgtggggagg | 2160 |
| atggggaatg tggggttaga tactcggcac cctggagctg cttgtctgag ctattatgac | 2220 |
| tgtgccgcgg tcatagtccg ttgtgtgttc ctctgacctt tgtgaggcag aactgatatt | 2280 |
| ttggtggtgg tagccttgtg cctccctttg tcctgttata attgtgttgc tctttattct | 2340 |

-continued

```
tagtctacgt ctatctttct ttggtagagg ttgcgtgctc gcatttgacc ttcaaatcta    2400
atagtttttc ctccaattgg agacgcttta ggattctaag agaaagcaag ctggaagggg    2460
tttccccttt aaattctaga aatgtggagt ctcagcccac ttaattttgc tcactcttaa    2520
aagcatttca accaaagcca ttcattaggg atttgatttg gagggcagga gggattccta    2580
tactgtttta agtgtgtatt aattctttca atttatcgaa ttatttagtg agtaacctgc    2640
tatgcactag gcactattct cggcttgtgg gtacagcagg aacagcaca gaccaaaatc     2700
tttgccttca ctgagcttat gggatagtgc tggtggtgga agtgcaacat attggtcaag    2760
tagaaaacaa gtgtgtggtt tttgtaaaaa attatttttt cctgatagct ggcccggtga    2820
tcatgtccat tgaggagaag atggaggctg atgcccgttc catctatgtt ggcaatgtga    2880
cgtactgggg ctctgactgg ggttgggggc aagttcttct tttggggaat tatttaatag    2940
tcctgaaaga acatctccgg gatagatgtg gttttgggtg tggagggagt gtgggaagga    3000
ggttaaaggt aatggaatga tcagtaatca gcaaaggctc tgggtttgga aggaaaagag    3060
attaattcct caaattacca gatttcatgt gctttggtgt atgatggccc agaccaaagg    3120
ctcgggaggg ttcttttgag acaggaattt gcctggtgcc tgtgaaattt ttctcctctc    3180
atcaggtgga ctatggtgca acagcagaag agctggaagc tcactttcat ggctgtggtt    3240
cagtcaaccg tgttaccata ctgtgtgaca aatttagtgg ccatcccaaa ggtaaagtaa    3300
aggggagtaa gttgagataa tttaaattac agtgtacaaa tagataaatt atgttttata    3360
ttgagcagta agttatttgg tgttaacaca ggtgatctgt gtcatttaag atcatggcat    3420
taatgttgat atatcaggag ttgcacctaa atgtcttcag aggccagata acaaaaatga    3480
aggctagatg tgggtgggat tacgaactag aaggggaggg gcagcttcta cttggcctat    3540
tatgcatat ggaaattcag gccctgtgtg tcttattttt acaaatttca aagagtagct     3600
ggaaatttta aaatttaaat gatttcgaat gattgaaatt ttccatttag aagaattttg    3660
acaaataaaa aatataactg cattgtagcc caaaacgaag catgcctgca ggttgaattt    3720
gacctgtgag gtatttgtaa cctcagagag atacaatgac aattcttttc aggtttgcgt    3780
atatagagtt ctcagacaaa gagtcagtga ggacttcctt ggcctagat gagtccctat     3840
ttagaggaag gcaaatcaag gtaagcctat gtccattgct gttctagttg tgtataaact    3900
ctccaggttg cctttaaggc tatcatttgt tcatctctga ctcaggtgat cccaaaacga    3960
accaacagac caggcatcag cacaacagac cggggttttc cacgagcccg ctaccgcgcc    4020
cggaccacca actacaacag ctcccgctct cgattctaca gtggttttaa cagcaggccc    4080
cggggtcgcg tctacaggtc aggatagatg ggctgctcct cttcccccg cctcccgtga     4140
gccccgtatg cttcctcctc tctggtctga ggaacctccc tcccccacc cctcccgtg     4200
gtcttcagga actttgtctc ctgcctgtgc aggttgagga aggtagttgc aggccaggcc    4260
agaaggcagc ctcatcatct tttctgcagt agaaattggt gataagggct gcatccctcc    4320
cttggttcaa agaggcttcc accccagcc tttttttttct tgggagttgg tggcatttga    4380
aggtgtttgc ggacaaaact gggaggaaca gggcctccag gaagttgaaa gcactgcttg    4440
gacatttgtt actttttttcg gagttaggga gggattgaag actgaacctc ccttggaaga   4500
ataccagagg ctagctagtt gatcctccca acagccttgt gggaggattt tgagatactt    4560
attctttatt tgagccagtc ttgcaaggtt aacttctcac tgggcctagt gtggtncccca   4620
ggttttgcc ttgcttcact tctgtctcta catttaaata gacgggttag gcatataaac     4680
cttggctttt cataagctct acctgcctat ccccaggagt tagggaggat ctatttgtga    4740
```

```
aggccctagg gtttaaaaac tgtggaggac tgaaaaactg gataaaaagg gggtcctttt      4800
ccttgcccct gtctctcact cagatgcgct tcttttcgc cactgtttgg caaagttttc       4860
tgttaagccc ccctcccct gccccagttc tcccaggtgc gttactattt ctgggatcat       4920
ggggtcggtt ttaggacact tgaacacttc ttttcccccc ttcccttcac agtaactggg      4980 gcagggcct acggggaggg gcttgtactg aactatctag tgatcacgtt aacacctaac       5040
tctccttctt tcttccaggg gccgggctag agcgacatca tggtattccc cttactaaaa     5100
aaagtgtgta ttaggaggag agagaggaaa aaagaggaa agaaggaaaa aaaaaagaat       5160
taaaaaaaaa aaaagaaaa acagaagatg accttgatgg aaaaaaaata ttttttaaaa      5220
aaaagatata ctgtgaagg ggggagaatc ccataactaa ctgctgagga gggacctgct      5280
ttggggagta ggggaaggcc cagggagtgg ggcaggggc tgcttattca ctctggggat      5340
tcgccatgga cacgtctcaa ctgcgcaagc tgcttgccca tgtttccctg ccccttcac      5400 cccttgggc ctgctcaagg gtaggtgggc gtggtggta ggaggttt ttttacccag         5460 ggctctggaa ggacaccaaa ctgttctgct tgttaccttc cctcccgtct tctcctcgcc     5520
tttcacagtc ccctcctgcc tgctcctgtc cagccaggtc taccacccac cccaccctc     5580 tttctccggc tccctgcccc tccagattgc ctggtgatct attttgtttc cttttgtgtt    5640 tcttttctg ttttgagtgt ctttcttgc aggtttctgt agccggaaga tctccgttcc      5700
gctcccagcg gctccagtgt aaattcccct tcccctggg gaaatgcact accttgtttt     5760 gggggtta gggtgtttt tgtttttcag ttgttttgtt ttttgtttt ttttttcc           5820 tttgccttt tccctttta tttggaggga atgggaggaa gtgggaacag ggaggtggga       5880
ggtggatttt gtttatttt ttagctcatt tccagggtg ggaatttttt tttaatatgt     5940
gtcatgaata aagttgtttt tgaaaataaa aaaaaaaaaa aaaaaaaa aaaaaaaaa         6000 aa                                                                     6002

<210> SEQ ID NO 19
<211> LENGTH: 19
<212> TYPE: DNA
<213> ORGANISM: Artificial Sequence
<220> FEATURE:
<223> OTHER INFORMATION: oligonucleotide

<400> SEQUENCE: 19
cgcagtgccc cgccttaga                                                   19

<210> SEQ ID NO 20
<211> LENGTH: 24
<212> TYPE: DNA
<213> ORGANISM: Artificial Sequence
<220> FEATURE:
<223> OTHER INFORMATION: oligonucleotide

<400> SEQUENCE: 20
acaagatggc gccgccgccc cggc                                             24

<210> SEQ ID NO 21
<211> LENGTH: 23
<212> TYPE: DNA
<213> ORGANISM: Artificial Sequence
```

-continued

```
<220> FEATURE:
<223> OTHER INFORMATION: oligonucleotide

<400> SEQUENCE: 21
cgcagtgccc cgccttagag gtg                                          23
```

SHORT GCG EXPANSIONS IN THE PAB II GENE FOR OCULOPHARYNGEAL MUSCULAR DYSTROPHY AND DIAGNOSTIC THEREOF

RELATED APPLICATION(S)

This application is a continuation claiming priority to International Application No. PCT/CA98/01133, filed Dec. 7, 1998 (designating the U.S.), which claims priority to Canadian Patent No. 2,218,199, filed Dec. 9, 1997, the entire teachings of both of which are incorporated herein by reference.

BACKGROUND OF THE INVENTION

1. Field of the Invention

The invention relates to PAB II gene, and its uses thereof for the diagnosis, prognosis and treatment of a disease related with protein accumulation in nucleus, such as oculopharyngeal muscular dystrophy.

2. Description of Prior Art

Autosomal dominant oculopharyngeal muscular dystrophy (OPMD) is an adult-onset disease with a world-wide distribution. It usually presents itself in the sixth decade with progressive swallowing difficulties (dysphagia), eye lid drooping (ptosis) and and proximal limb weakness. Unique nuclear filament inclusions in skeletal muscle fibers are its pathological hallmark (Tome, F.M.S. & Fardeau, Acta Neuropath. 49, 85–87 (1980)). Using the full power of linkage analysis in eleven French Canadian families, the oculopharyngeal muscular dystrophy gene was fine mapped on human chromosome 14 (Brais et al., 1997, Neuromuscular Disorders 7 (Suppl.1):S70–74). A region of 0.75 cM was thereby identified as a region containing the potential and unknown OMPD gene (Brais et al., 1997, supra). Unfortunately, the OMPD gene has yet to be isolated and its nucleic acid or protein sequence have yet to be described.

It would be highly desirable to be provided with a tool for the diagnosis, prognosis and treatment of a disease related with polyalanine accumulation in the nucleus, such as observed in oculopharyngeal muscular dystrophy.

SUMMARY OF THE INVENTION

One aim of the present invention is to provide a tool for the diagnosis, prognosis and treatment of a disease related with polyalanine accumulation in nucleus, such as oculopharyngeal muscular dystrophy.

Herein, the poly(A) binding protein II (PAB II) gene was isolated from a 217 kb candidate interval in chromosome 14q11. A (GCG)6 repeat encoding a polyalanine tract located at the N-terminus of the protein was expanded to (GCG)8–13 in the 144 OPMD families screened. More severe phenotypes were observed in compound heterozygotes for the (GCG)9 mutation and a (GCG)7 allele found in 2% of the population, whereas homozygosity for the (GCG)7 allele leads to autosomal recessive OPMD. Thus the (GCG)7 allele is an example of a polymorphism which can act as either a modifier of a dominant phenotype or as a recessive mutation. Pathological expansions of the polyalanine tract may cause mutated PAB II oligomers to accumulate as filament inclusions in nuclei.

In accordance with the present invention there is provided a human PAB II gene containing a transcribed polymorphic GCG repeat, which comprises a sequence as set forth in FIG. 4, which includes introns and flanking genomic sequence.

The allelic variants of GCG repeat of the human PAB II gene are associated with a disease related with protein accumulation in the nucleus, such as polyalanine accumulation, or with a disease related with swallowing difficulties, such as oculopharyngeal muscular dystrophy.

In accordance with the present invention there is also provided a method for the diagnosis of a disease associated with protein accumulation in the nucleus, which comprises the steps of:

a) obtaining a nucleic acid sample of said patient; and b) determining allelic variants of a GCG repeat of the human PAB II gene; whereby long allelic variants are indicative of a disease related with protein accumulation in the nucleus, such as polyalanine accumulation and oculopharyngeal muscular dystrophy.

The long allelic variants have from about 245 to about 263 bp in length.

In accordance with the present invention there is also provided a non-human mammal model for the human PAB II gene, whose germ cells and somatic cells are modified to express at least one allelic variant of the PAB II gene and wherein said allelic variant of the PAB II is being introduced into the mammal, or an ancestor of the mammal, at an embryonic stage.

In accordance with the present invention there is also provided a method for the screening of therapeutic agents for the prevention and/or treatment of oculopharyngeal muscular dystrophy, which comprises the steps of:

a) administering the therapeutic agents to the non-human animal of the present invention or oculopharyngeal muscular dystrophy patients; and b) evaluating the prevention and/or treatment of development of oculopharyngeal muscular dystrophy in this animal (such as a mammal) or in patients.

In accordance with the present invention there is also provided a method to identify genes, products thereof, or part thereof, which interact with a biochemical pathway affected by the PAB II gene, which comprises the steps of:

a) designing probes and/or primers using the PAB II gene and screening oculopharyngeal muscular dystrophy patients samples with said probes and/or primers; and b) evaluating the role of the identified gene in oculopharyngeal muscular dystrophy patients.

BRIEF DESCRIPTION OF THE DRAWINGS

FIGS. 4A–4E illustrate the nucleotide sequence of human poly(A) binding protein II (hPAB II) (SEQ ID NO:18).

DETAILED DESCRIPTION OF THE INVENTION

Figure 1A:
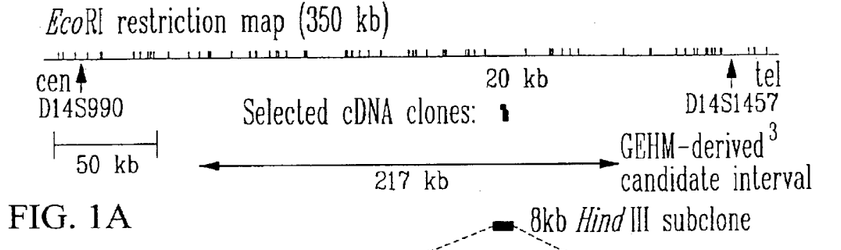
FIGS. 1A–1B illustrate the positional cloning of the PAB II gene.

In order to identify the gene mutated in OPMD, a 350 kb cosmid contig was constructed between flanking markers D14S990 and D14S1457 (FIG. 1A). Positions of the PAB II-selected cDNA clones were determined in relation to the EcoRI restriction map and the Genealogy-based Estimate of Historical Meiosis (GEHM)-derived candidate interval (Ronmmens, J. M. et al., in Proceedings of the third international workshop on the identification of transcribed sequences (eds. Hochgeschwender, U. & Gardiner, K.) 65–79 (Plenum, New York, 1994)).

The human poly(A) binding protein II gene (PAB II) is encoded by the nucleotide sequence as set forth in FIG. 4.

Twenty-five cDNAs were isolated by cDNA selection from the candidate interval (Rommens, J. M. et al., in Proceedings of the third international workshop on the identification of transcribed sequences (eds. Hochgeschwender, U. & Gardiner, K.; 65–79; Plenum, New York, 1994). Three of these hybridized to a common 20 kb EcoRI restriction fragment and showed high sequence homology to the bovine poly(A) binding protein II gene (bPAB II) (FIG. 1A). The PAB II gene appeared to be a good candidate for OPMD because it mapped to the genetically defined 0.26 cM candidate interval in 14q11 (FIG. 1A), its mRNA showed a high level of expression in skeletal muscle, and the PAB II protein is exclusively localized to the nucleus (Krause, S. et al., Exp. Cell Res. 214, 75–82 (1994)) where it acts as a factor in mRNA polyadenylation (Whale, E., Cell 66, 759–768 (1991); Whale, E. et al., J. Biol. Chem. 268, 2937–2945 (1993); Bienroth, S. et al., EMBO J. 12, 585–594 (1993)).

Figure 1B:
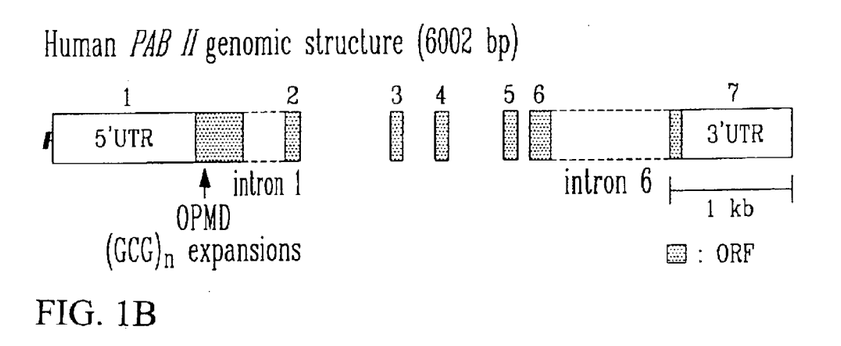

A 8 kb HindIII genomic fragment containing the PAB II gene was subcloned and sequenced (6002 bp; GenBank: AF026029) (Nemeth, A. et al., Nucleic Acids Res. 23, 4034–4041 (1995)) (FIG. 1B). Genomic structure of the PAB II gene, and position of the OPMD (GCG)n expansions. Exons are numbered. Introns 1 and 6 are variably present in 60% of cDNA clones. ORF, open reading frame; cen, centromere and tel, telomere.

The coding sequence was based on the previously published bovine sequence (GenBank: X89969) and the sequence of 31 human cDNAs and ESTs. The gene is composed of 7 exons and is transcribed in the cen-qter orientation (FIG. 1B). Multiple splice variants are found in ESTs and on Northern blots (Nemeth, A. et al., Nucleic Acids Res. 23, 4034–4041 (1995)). In particular, introns 1 and 6 are present in more than 60% of clones (FIG. 1B)(Nemeth, A. et al., Nucleic Acids Res. 23, 4034–4041 (1995)). The coding and protein sequences are highly conserved between human, bovine and mouse (GenBank: U93050). 93% of the PAB II sequence was readily amenable to RT-PCR- or genomic-SSCP screening. No mutations were uncovered using both techniques. However, a 400 bp region of exon 1 containing the start codon could not be readily amplified. This region is 80% GC rich. It includes a (GCG)6 repeat which codes for the first six alanines of a homopolymeric stretch of 10 (FIG. 2G). Nucleotide sequence of the mutated region of PAB II as well as the amino acid sequences of the N-terminus polyalanine stretch and position of the OPMD alanine insertions is also shown in FIG. 2.

Special conditions were designed to amplify by PCR a 242 bp genomic fragment including this GCG-repeat. The (GCG)6 allele was found in 98% of French Canadian non-OPMD control chromosomes, whereas 2% of chromosomes carried a (GCG)7 polymorphism (n=86) (Brais, B. et al., Hum. Mol. Genet. 4, 429–434 (1995)).

Figure 2A:
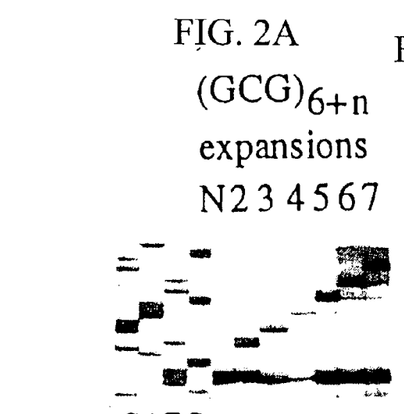
FIGS. 2A–2G illustrate the OPMD (GCG)n expansion sizes and sequence of the mutation site (SEQ ID NO: 1nucleic acid mutation site; SEQ ID NO:2: nucleic acid mutation site without insertion; SEQ ID NO:3–9, nucleic acid mutation site with 1 through 7 (GCG) insertions, respectively; SEQ ID NO:10, amino acid sequence encoded by the nucleic acid mutation site; SEQ ID NO: 11–17, amino acid sequence encoded by the nucleic acid mutation site with 1 through 7 Alanine insertions, respectively)
Figure 2B:
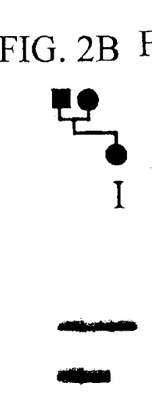

Screening OPMD cases belonging to 144 families showed in all cases a PCR product larger by 6 to 21 bp than that found in controls (FIG. 2A). (GCG)6 normal allele (N) and the six different (GCG)n expansions observed in 144 families.

Sequencing of these fragments revealed that the increased sizes were due to expansions of the GCG repeat (FIG. 2G). FIG. 2F shows the sequence of the (GCG)9 French Canadian expansion in a heterozygous parent and his homozygous child. Partial sequence of exon 1 in a normal (GCG)6 control (N), a heterozygote (ht.) and a homozygote (hm.) for the (GCG)9-repeat mutation. The number of families sharing the different (GCG)n-repeats expansions is shown in Table 1.

TABLE 1

Number of families sharing the different dominant (GCG)n OPMD mutations

| Mutations | Polyalanine† | Families |
|---|---|---|
| (GCG)8 | 12 | 4 |
| (GCG)9 | 13 | 99 |
| (GCG)10 | 14 | 19 |
| (GCG)11 | 15 | 16 |
| (GCG)12 | 16 | 5 |
| (GCG)13 | 17 | 1 |
| Total | | 144 |

†, 10 alanine residues in normal PAB II.

Figure 2C:
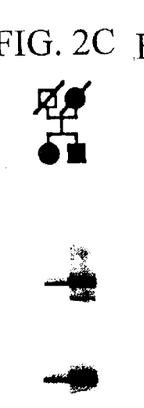

The (GCG)9 expansion shared by 70 French Canadian families is the most frequent mutation we observed (Table 1) The (GCG)9 expansion is quite stable, with a single doubling observed in family F151 in an estimated 598 French Canadian meioses (FIG. 2C). The doubling of the French Canadian (GCG)9 expansion is demonstrated in Family F151.

This contrasts with the unstable nature of previously described disease-causing triplet repeats (Rosenberg, R. N., New Eng. J. Med. 335, 1222–1224 (1996)).

Figure 2D:
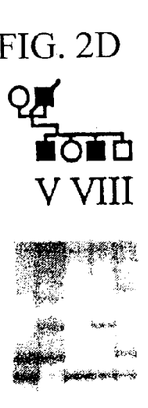
Figures 2E, 2F:
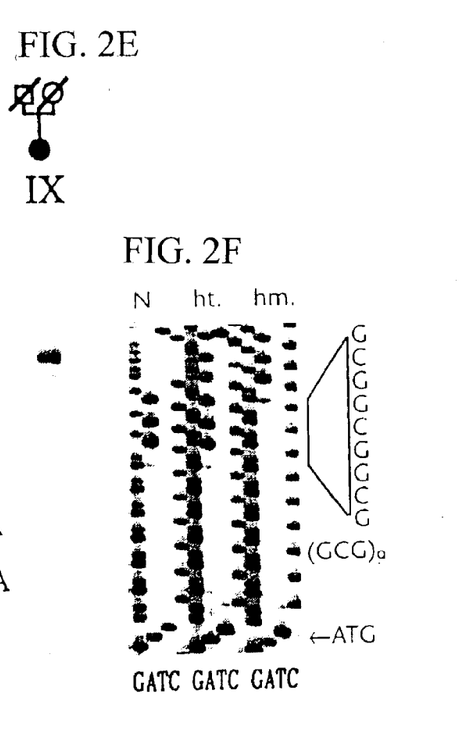
Figure 2G:
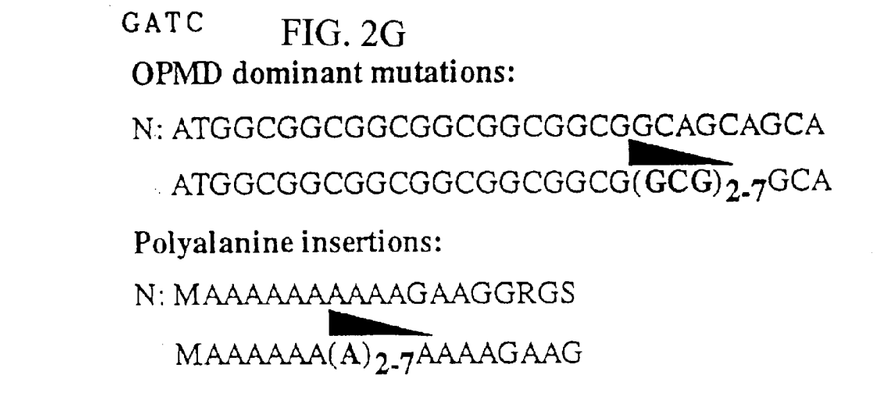

Genotyping of all the participants in the clinical study of French Canadian OPMD provided molecular insights into the clinical variability observed in this condition. The genotypes for both copies of the PAB II mutated region were added to an anonymous version of this clinical database of 176 (GCG)9 mutation carriers (Brais, B. et al., Hum. Mol. Genet. 4, 429–434 (1995)). Severity of the phenotype can be assessed by the swallowing time (st) in seconds taken to drink 80 cc of ice-cold water (Brais, B. et al., Hum. Mol. Genet. 4, 429–434 (1995); Bouchard, J.-P. et al., Can. J. Neurol. Sci. 19, 296–297 (1992)). The late onset and progressive nature of the muscular dystrophy is clearly illustrated in heterozygous carriers of the (GCG)9 mutation (bold curve in FIG. 3) when compared to the average st of control (GCG)6 homozygous participants(n=76, thinner line in FIG. 3). The bold curve represents the average OPMD st for carriers of only one copy of the (GCG)9 mutation (n=169), while the thinner line corresponds to the average st for (GCG)6 homozygous normal controls (n=76). The black dot corresponds to the st value for individual VIII. Roman numerals refer to individual cases shown in FIGS. 2B, 2D and discussed in the text. The genotype of a homozygous (GCG)9 patient and her parents is shown in FIG. 2B. Independent segregation of the (GCG)7 allele is also shown. Of note, case V has a more severe OPMD phenotype (FIG. 2D).

Figure 3:
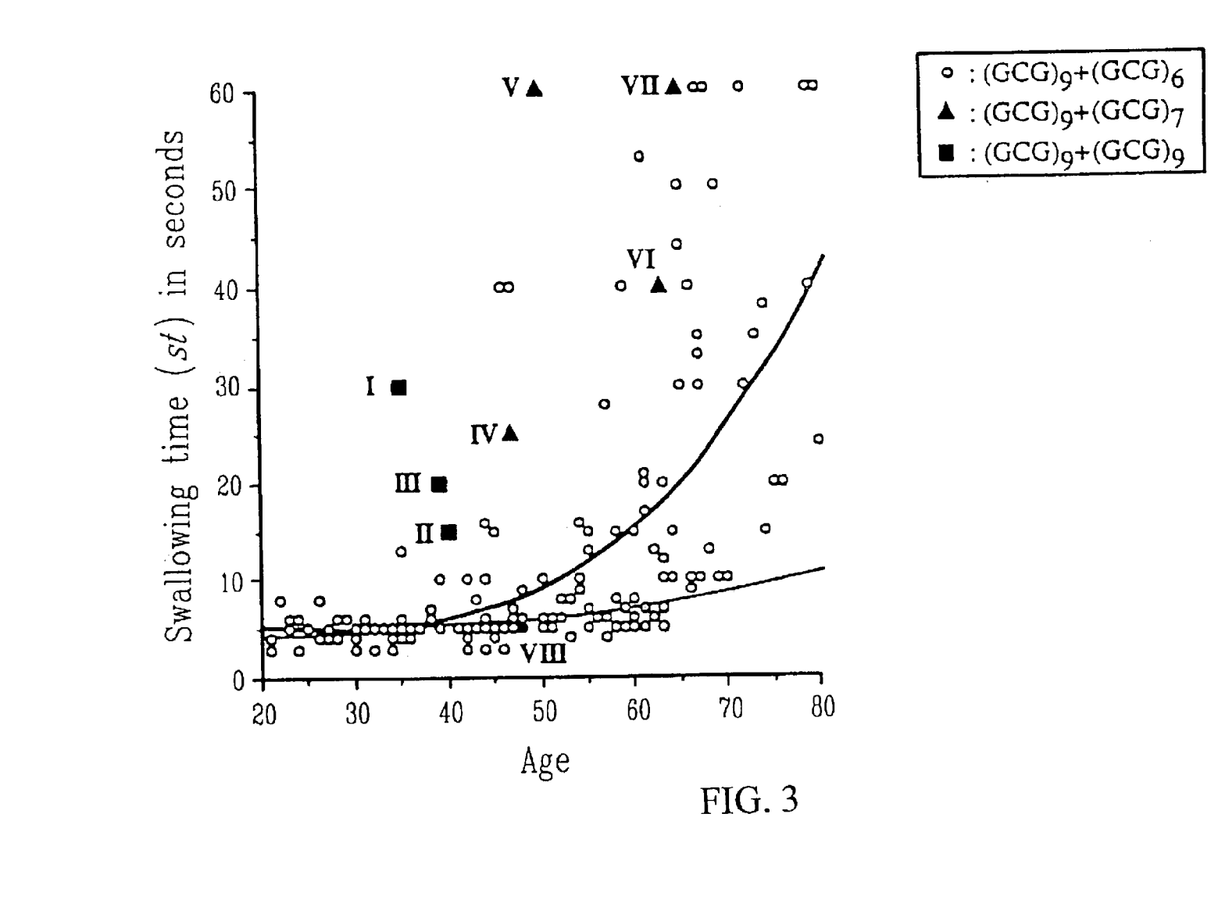
FIG. 3 illustrates the age distribution of swallowing time (st) for French Canadian OPMD carriers of the (GCG)9 mutation.
Figure 4A:
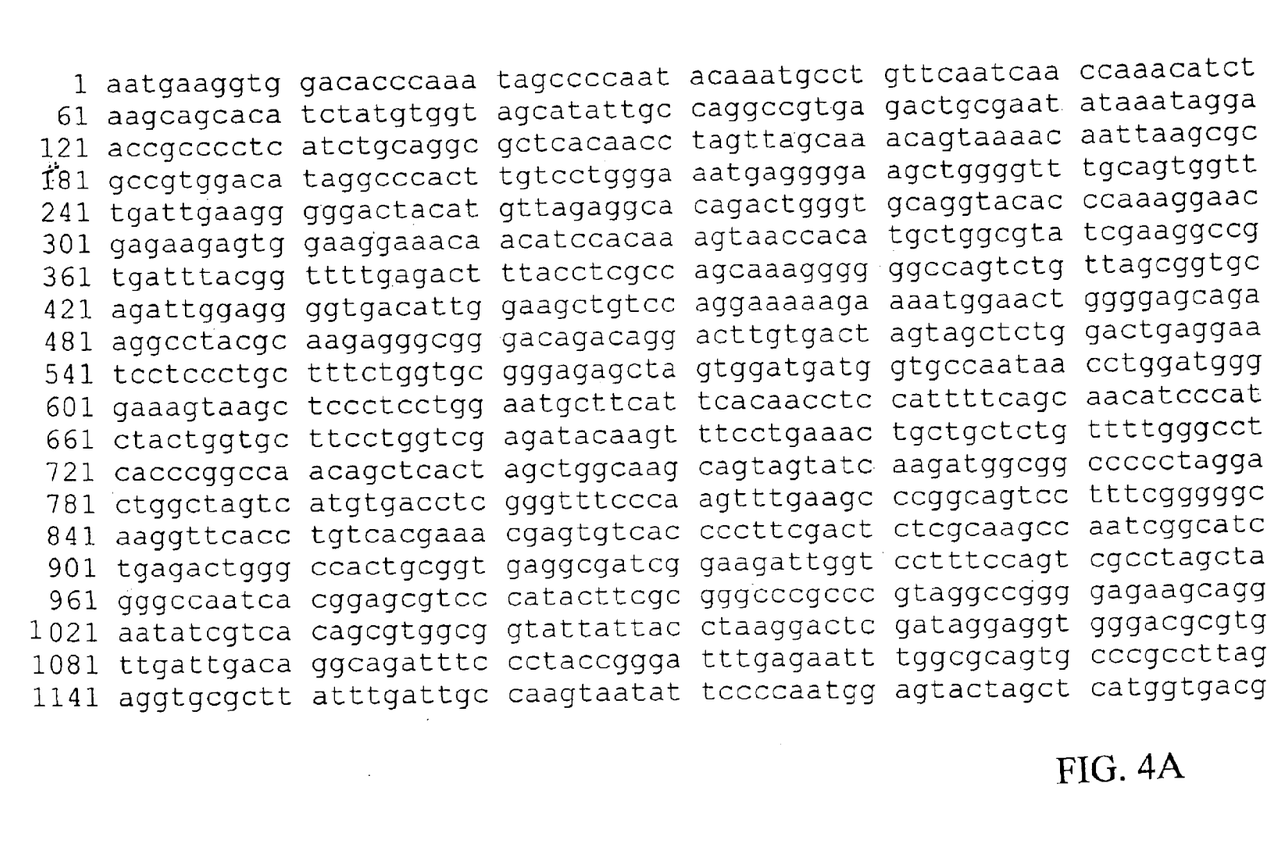
Figure 4B:
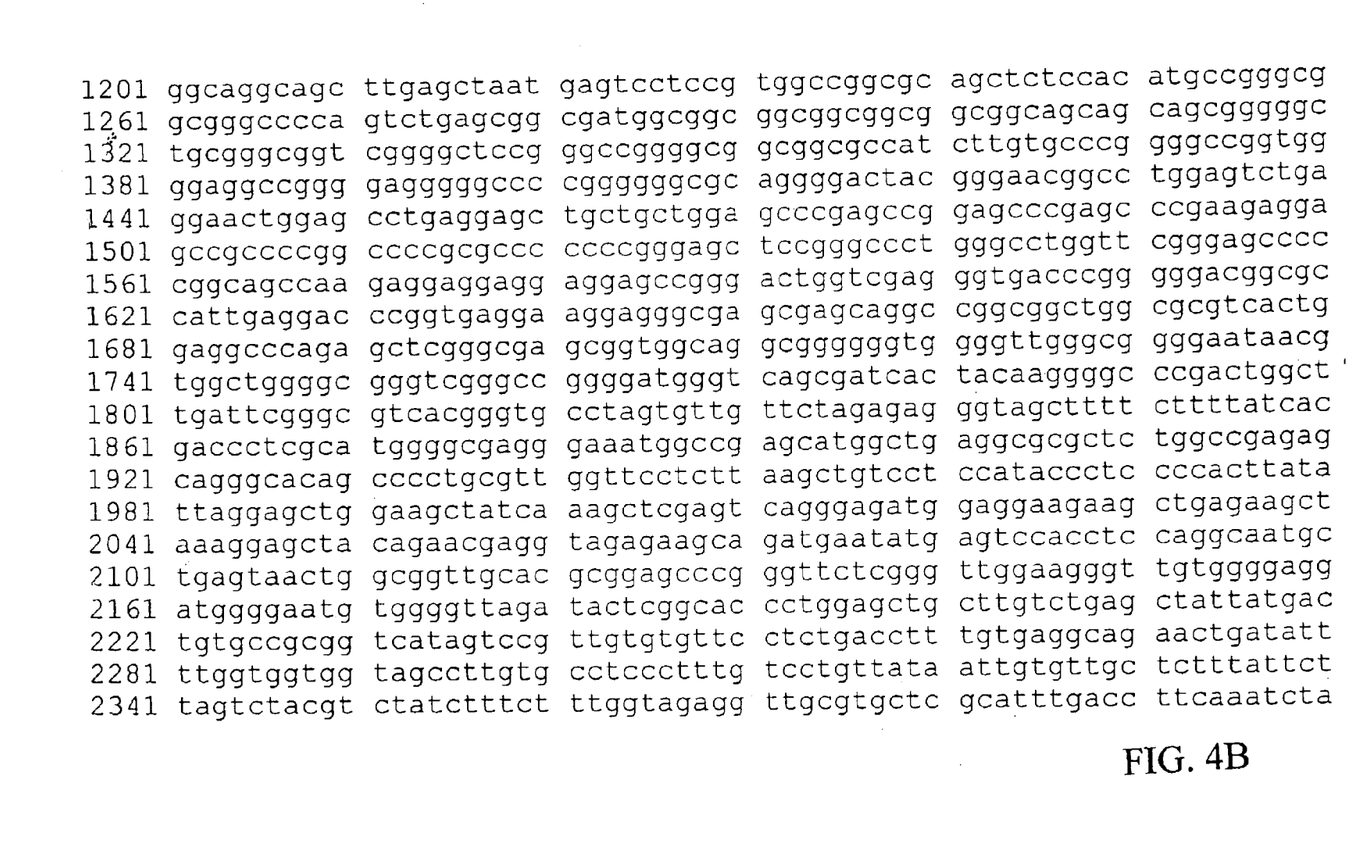
Figure 4C:
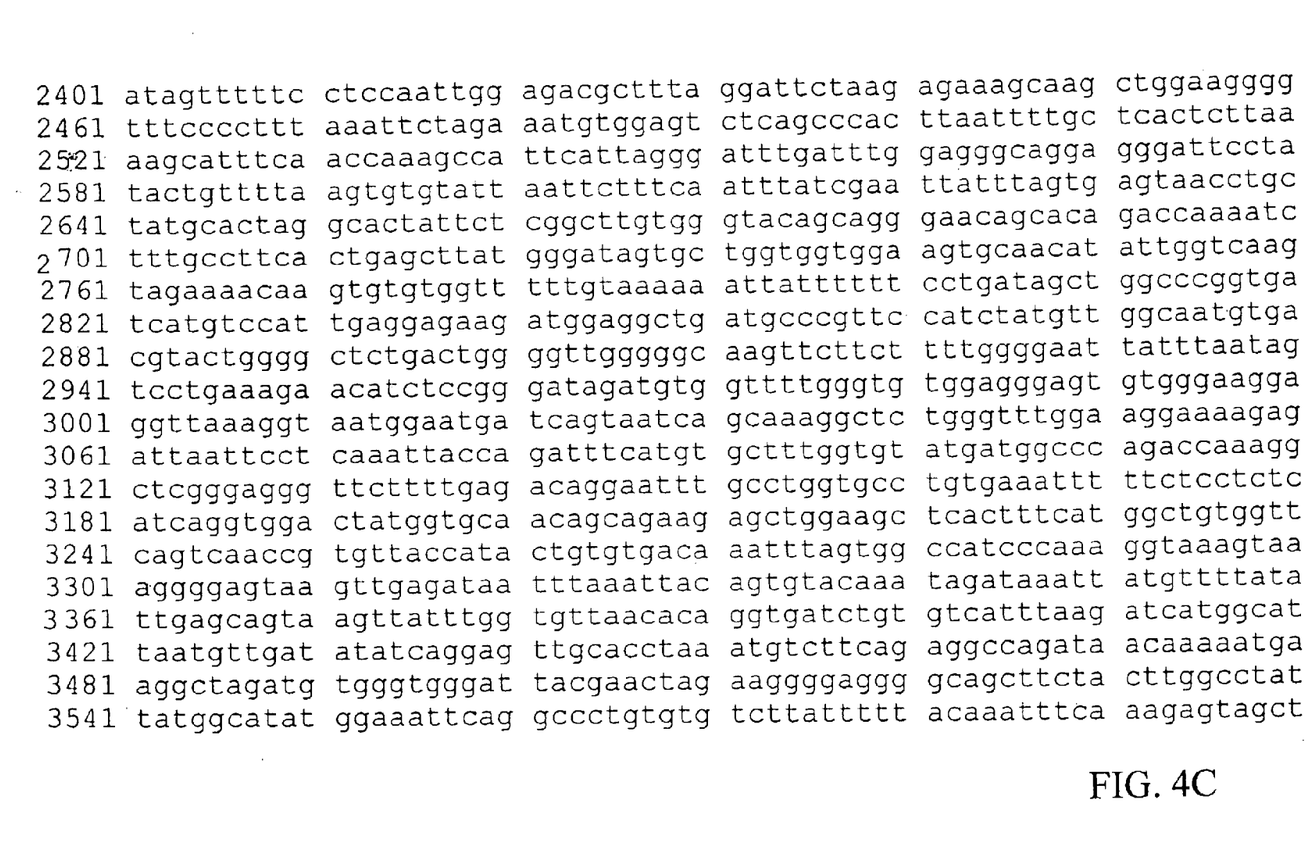
Figure 4D:
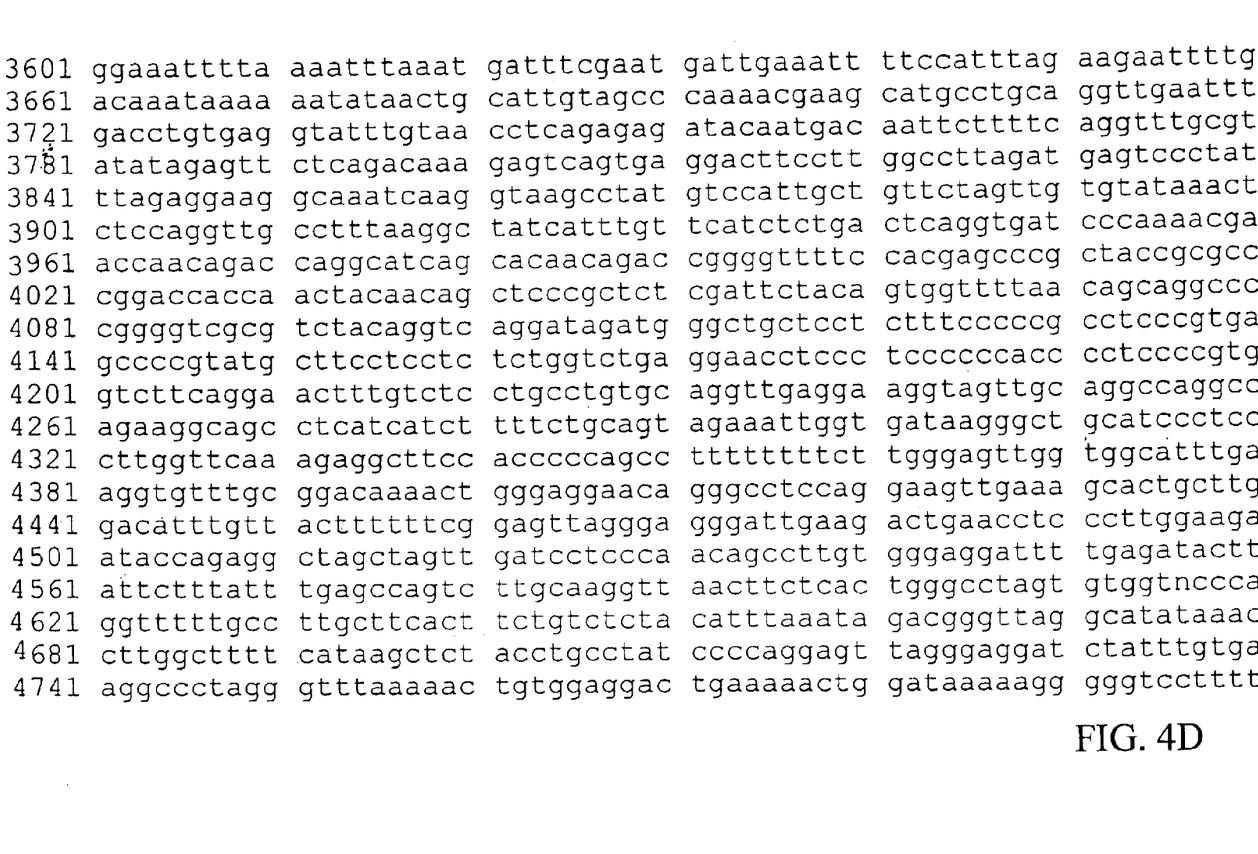

Two groups of genotypically distinct OPMD cases have more severe swallowing difficulties. Individuals I, II, and III have an early-onset disease and are homozygous for the (GCG)9 expansion (P<10–5) (FIGS. 2B, F). Cases IV, V, VI and VII have more severe phenotypes and are compound heterozygotes for the (GCG)9 mutation and the (GCG)7 polymorphism (P<10–5). In FIG. 2D the independent segregation of the two alleles is shown. Case V, who inherited the French Canadian (GCG)9 mutation and the (GCG)7 polymorphism, is more symptomatic than his brother VIII who carries the (GCG)9 mutation and a normal (GCG)6 allele (FIGS. 2D and 3). The (GCG)7 polymorphism thus appears to be a modifier of severity of dominant OPMD. Furthermore, the (GCG)7 allele can act as a recessive mutation. This was documented in the French patient IX who inherited two copies of the (GCG)7 polymorphism and has a late-onset autosomal recessive form of OPMD (FIG. 2E). Case IX, who has a recessive form of OPMD, is shown to have inherited two copies of the (GCG)7 polymorphism.

This is the first description of short trinucleotide repeat expansions causing a human disease. The addition of only two GCG repeats is sufficient to cause dominant OPMD. OPMD expansions do not share the cardinal features of "dynamic mutations". The GCG expansions are not only short they are also meiotically quite stable. Furthermore, there is a clear cut-off between the normal and abnormal alleles, a single GCG expansion causing a recessive phenotype. The PAB II (GCG)7 allele is the first example of a relatively frequent allele which can act as either a modifier of a dominant phenotype or as a recessive mutation. This dosage effect is reminiscent of the one observed in a homozygote for two dominant synpolydactyly mutations. In this case, the patient had more severe deformities because she inherited two duplications causing an expansion in the polyalanine tract of the HOXD13 protein (Akarsu, A. N. et al., Hum. Mol. Genet. 5, 945–952 (1996)). A duplication causing a similar polyalanine expansion in the a subunit 1 gene of the core-binding transcription factor (CBF(1) has also been found to cause dominant cleido-cranial dysplasia (Mundlos, S. et al., Cell 89, 773–779 (1997)). The mutations in these two rare diseases are not triplet repeats. The are duplications of "cryptic repeats" composed of mixed synonymous codons and are thought to result from unequal crossing over (Warren, S. T., Science 275, 408–409 (1997)). In the case of OPMD, slippage during replication causing a reiteration of the GCG codon is a more likely mechanism (Wells, D. R., J. Biol. Chem. 271, 2875–2878 (1996)).

Different observations converge to suggest that a gain of function of PAB II may cause the accumulation of nuclear filaments observed in OPMD (Tome, F. M. S. & Fardeau, Acta Neuropath. 49, 85–87 (1980)). PAB II is found mostly in dimeric and oligomeric forms (Nemeth, A. et al., Nucleic Acids Res. 23, 4034–4041 (1995)). It is possible that the polyalanine tract plays a role in polymerization. Polyalanine stretches have been found in many other nuclear proteins such as the HOX proteins, but their function is still unknown (Davies, S. W. et al., Cell 90, 537–548 (1997)). Alanine is a highly hydrophobic amino acid present in the cores of proteins. In dragline spider silk, polyalanine stretches are thought to form P-sheet structures important in ensuring the fibers' strength (Simmons, A. H. et al., Science 271, 84–87 (1996)). Polyalanine oligomers have also been shown to be extremely resistant to chemical denaturation and enzymatic degradation (Forood, B. et al., Bioch. and Biophy. Res. Corn. 211, 7–13 (1995)). One can speculate that PAB II oligomers comprised of a sufficient number of mutated molecules might accumulate in the nuclei by forming undegradable polyalanine rich macromolecules. The rate of the accumulation would then depend on the ratio of mutated to non-mutated protein. The more severe phenotypes observed in homozygotes for the (GCG)9 mutations and compound heterozygotes for the (GCG)9 mutation and (GCG)7 allele may correspond to the fact that in these cases PAB II oligomers are composed only of mutated proteins. The ensuing faster filament accumulation could cause accelerated cell death. The recent description of nuclear filament inclusions in Huntington's disease, raises the possibility that "nuclear toxicity" caused by the accumulation of mutated homopolymeric domains is involved in the molecular pathophysiology of other triplet repeats diseases (Davies, S. W. et al., Cell 90, 537–548 (1997); Scherzinger, E. et al., Cell 90, 549–558 (1997); DiFiglia, M. et al., Science 277, 1990–1993 (1997)). Future immunocytochemical and expression studies will be able to test this pathophysiological hypothesis and provide some insight into why certain muscle groups are more affected while all tissues express PAB II.

Methods

Contig and cDNA Selection

The cosmid contig was constructed by standard cosmid walking techniques using a gridded chromosome 14specific cosmid library (Evans, G. A. et al., Gene 79, 9–20 (1989)). The cDNA clones were isolated by cDNA selection as previously described (Rommens, J. M. et al., in Proceedings of the third international workshop on the identification of transcribed sequences (eds. Hochgeschwender, U. & Gardiner, K.) 65–79 (Plenum, New York, 1994)).

Three cDNA clones corresponding to PAB II were sequenced (Sequenase, USB). Clones were verified to map to cosmids by Southern hybridization. The 8 kb HindIII restriction fragment was subcloned from cosmid 166G8 into pBluescriptII (SK) (Stratagene). The clone was sequenced using primers derived from the bPABII gene and human EST sequences. Sequencing of the PAB II introns was done by primer walking.

PAB II Mutation Screening and Sequencing

All cases were diagnosed as having OPMD on clinical grounds (Brais, D. et al., Hum. Mol. Genet. 4, 429–434 (1995)). RT-PCR and genomic SSCP analyses were done using standard protocols (Lafrenière, R. G. et al., Nat. Genet. 15, 298–302 (1997)). The primers used to amplify the PAB II mutated region were: 5'-CGCAGTGCCCCGCCTTAGA-3' (SEQ ID NO:4) and 5'-ACAAGATGGCGCC-GCCGCCCCGGC-3' (SEQ ID NO:5). PCR reactions were performed in a total volume of 15 $\mu$l containing: 40 ng of genomic DNA; 1.5 $\mu$g of BSA; 1 $\mu$M of each primer; 250 $\mu$M dCTP and dTTP; 25 $\mu$M dATP; 125 $\mu$M of dGTP and 125 $\mu$M of 7-deaza-dGTP (Pharmacia); 7.5% DMSO; 3.75 $\mu$Ci [$^{35}$S]dATP, 1.5 unit of Taq DNA polymerase and 1.5 mM MgC12 (Perkin Elmer). For non-radioactive PCR reactions the [$^{35}$S]dATP was replaced by 225 $\mu$M of dATP. The amplification procedure consisted of an initial denaturation step at 95° C. for five minutes, followed by 35 cycles of denaturation at 95° C. for 15 s, annealing at 70° C. for 30 s, elongation at 74° C. for 30 s and a final elongation at 74° C. for 7 min. Samples were loaded on 5% polyacrylamide denaturing gels. Following electrophoresis, gels were dried and autoradiographs were obtained. Sizes of the inserts were determined by comparing to a standard M13 sequence (Sequenase™, USB). Fragments used for sequencing were gel-purified. Sequencing of the mutated fragment using the Amplicycle kit™(Perkin Elmer) was done with the 5'-CGCAGTGCCCCGCCTTAGAGGTG-3' (SEQ ID NO:6) primer at an elongation temperature of 68° C.

Stability of (GCG)-repeat Expansions

The meiotic stability of the (GCG)9-repeat was estimated based on a large French Canadian OPMD cohort. It had been previously established that a single ancestral OPMD carrier chromosome was introduced in the French Canadian population by three sisters in 1648. Seventy of the seventy one French Canadian OPMD families tested to date segregate a (GCG)9 expansion. However, in family F151, the affected brother and sister, despite sharing the French Canadian ancestral haplotype, carry a (GCG)12 expansion, twice the size of the ancestral (GCG)9 mutation (FIG. 2C). In this founder effect study, it is estimated that 450 (304–594) historical meioses shaped the 123 OPMD cases belonging to 42 of the 71 enrolled families. The screening of the full set of participants allowed an identification of another 148 (GCG)9 carrier chromosomes. Therefore, it is estimated that a single mutation of the (GCG)9 expansion has occurred in 598 (452–742) meioses.

Genotype-phenotype Correlations 176 carriers of at least one copy of the (GCG)9 mutation were examined during the early stage of the linkage study. All were asked to swallow 80 cc of ice-cold water as rapidly as possible. Testing was stopped after 60 seconds. The swallowing time (st) was validated as a sensitive test to identify OPMD cases (Brais, B. et al., Hum. Mol. Genet. 4, 429–434 (1995); Bouchard, J.-P. et al., Can. J. Neurol. Sci. 19, 296–297 (1992)). The st values for 76 (GCG)6 homozygotes normal controls is illustrated in FIG. 3. Analyses of variance were computed by two-way ANOVA (SYSTAT package). For the (GCG)9 homozygotes their mean st value was compared to the mean value for all (GCG)9 heterozygotes aged 35–40 ($P<10^{-5}$). For the (GCG)9 and (GCG)7 compound heterozygotes their mean st value was compared to the mean value for all (GCG)9 heterozygotes aged 45–65 ($P<10^{-5}$).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated nucleic acid sequence comprising a polymorphic GCG repeat of exon I of a human PAB II gene, wherein said polymorphic GCG repeat has the sequence ATG (GCG)6+n GCA, with n being selected from 1 to 7 and wherein said polymorphic repeat of said GCG repeat in a patient's human PAB II gene is indicative of a disease in said human patient.

2. The nucleic acid sequence of claim 1, wherein n is selected from 2 to 7, and wherein said polymorphic repeat of said GCG repeat is associated with an increased severity of said disease.

3. A method for the diagnosis or prognosis of oculopharyngeal muscular dystrophy (OPMD), a disease associated with protein accumulation in a cell nucleus, and/or swallowing difficulty and/or ptosis in a human patient, which comprises:

a) obtaining a nucleic acid sample of said patient; and
   b) determining allelic variants of a GCG repeat in exon I of the PAB II gene, said GCG repeat having the sequence ATG (GCG)6+n GCA, wherein n is selected from 0 to 7, and
   whereby at least one of the two alleles of said GCG repeat having an n equal to 1 to 7, is indicative of OPMD.

4. The method of claim 3, wherein n is selected from 2 to 7, and wherein said allelic variant is associated with an increased severity of said disease.

5. The method of claim 3, wherein said first allele of said GCG repeat has an n which is equal to 1.

6. The method of claim 5, wherein said second allele of said GCG repeat has an n selected from 2 to 7, and wherein said first allele is a modulator of the severity of the phenotype associated with said second allele.

7. An isolated PAB II nucleic acid sequence comprising a polymorphic GCG repeat having the sequence ATG (GCG)6+n GCA, wherein n is selected from the group consisting of:

a) n=0, wherein said nucleic acid sequence is associated with a non-disease phenotype; and
   b) n is selected from 1 to 7, wherein said nucleic acid sequence is associated with a phenotype of oculopharyngeal muscular dystrophy, selected from at least one of protein accumulation in a cell nucleus, swallowing difficulty, and ptosis.

8. The isolated nucleic acid sequence of claim 7, wherein n=0, and wherein said sequence comprises the sequence as set forth in SEQ ID NO:18.

9. The isolated nucleic acid sequence of claim 7, wherein n=0, and wherein said sequence comprises the sequence as set forth in SEQ ID NO:1.

10. The isolated nucleic acid sequence of claim 7, wherein n=0, and wherein said GCG repeat has the sequence set forth in SEQ ID NO:2.

11. The isolated nucleic acid sequence of claim 7, wherein n=1, and wherein said GCG repeat has the sequence set forth in SEQ ID NO:3.

12. The isolated nucleic acid sequence of claim 7, wherein n=2, and wherein said GCG repeat has the sequence set forth in SEQ ID NO:4.

13. The isolated nucleic acid sequence of claim 7, wherein n=3, and wherein said GCG repeat has the sequence set forth in SEQ ID NO:5.

14. The isolated nucleic acid sequence of claim 7, wherein n=4, and wherein said GCG repeat has the sequence set forth in SEQ ID NO:6.

15. The isolated nucleic acid sequence of claim 7, wherein n=5, and wherein said GCG repeat has the sequence set forth in SEQ ID NO:7.

16. The isolated nucleic acid sequence of claim 7, wherein n=6, and wherein said GCG repeat has the sequence set forth in SEQ ID NO:8.

17. The isolated nucleic acid sequence of claim 7, wherein n=7, and wherein said GCG repeat has the sequence set forth in SEQ ID NO:9.

* * * * *